United States Patent
Addiego et al.

(10) Patent No.: US 6,461,995 B1
(45) Date of Patent: Oct. 8, 2002

(54) EXTRUDED HONEYCOMB DEHYDROGENATION CATALYST AND METHOD

(75) Inventors: William P. Addiego, Big Flats, NY (US); Wei Liu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/566,544

(22) Filed: May 8, 2000

(51) Int. Cl.[7] .......................... B01J 23/00; B01J 23/58; B01J 23/70; B01J 31/00; B32B 3/12
(52) U.S. Cl. ........................ 502/304; 502/159; 502/313; 502/321; 502/328; 502/330; 502/338; 502/527.11; 502/527.19; 502/527.24; 428/116
(58) Field of Search .................................. 502/338, 330, 502/304, 313, 321, 328, 527.11, 527.19, 527.24, 159; 428/116

(56) References Cited

U.S. PATENT DOCUMENTS

| 4,711,930 A |   | 12/1987 | Hoelderich et al. .......... 502/209 |
| 5,097,091 A |   | 3/1992  | Kremer et al. ............... 585/444 |
| 5,168,085 A | * | 12/1992 | Addiego et al. ............... 502/66 |
| 5,258,348 A | * | 11/1993 | Van Buren et al. ......... 502/328 |

* cited by examiner

Primary Examiner—Mark L. Bell
Assistant Examiner—Patricia L. Hailey
(74) Attorney, Agent, or Firm—Kees van der Sterre

(57) ABSTRACT

Extruded honeycomb dehydrogenation catalysts of high structural integrity, composed of potassium oxide (carbonate)-promoted oxide-stabilized iron oxides and having a honeycomb cell density in the range of 15–400 channels per square inch, a channel wall thickness in the range of 0.2–3 mm, and an axial crushing strength in excess of 100 psi, are prepared from extrusion batches incorporating polymer binders exhibiting improved compatibility with high batch concentrations of dissolved catalyst precursors or constituents.

9 Claims, No Drawings

EXTRUDED HONEYCOMB DEHYDROGENATION CATALYST AND METHOD

BACKGROUND OF THE INVENTION

This invention relates to extruded honeycomb catalysts, and more particularly to a method for making improved catalysts for the catalytic dehydrogenation of hydrocarbons.

One dehydrogenation reaction of particular commercial interest is the dehydrogenation of ethylbenzene to styrene:

Ethylbenzene⇌$H_2$+Styrene

Dehydrogenation of ethylbenzene is a major petrochemical process for styrene monomer production. In this process, deep conversion to styrene is limited by thermodynamic equilibrium:

$$K_P = \frac{x_{H2} \cdot x_{ST}}{x_{EB}} \cdot P$$

wherein $x_i$ are the molar fractions of the reactants and product and P corresponds to the total pressure within the reactor. This process is typically carried out in a packed bed reactor in the gas phase, with high conversion to styrene being favored by low reactor pressures and high temperatures.

When ethylbenzene dehydrogenation is run using a conventional catalyst pellet bed (e.g., beds made up of ⅛" cylinders of the catalyst), large pressure drops across the reactor significantly limit reactor utilization efficiency. Increasing pellet size to reduce pressure drop is not a viable solution in this case since efficient mass and heat transfer within the catalyst bed require small catalyst pellet sizes. Thus conventional pellet beds cannot meet both low reactor pressure drop and high mass/heat transfer requirements.

Attempts to solve this problem have included both different pellet configurations and the substitution of honeycomb catalysts for the pellets. U.S. Pat. No. 5,097,091 describes toothed-wheel shaped catalyst pellets designed to improve reactor efficiency, but such pellets do not fundamentally change the nature of the back-pressure problem.

The potential advantages that could be realized through the use of an effective honeycomb catalyst for styrene processing are several. First, a catalyst offering large geometric surface areas, short diffusion paths within the thin channels walls, and straight thin channels of low back-pressure could in principle lead to increases in both catalytic activity and styrene selectivity. In addition, the development of a durable honeycomb catalyst could permit easy installation and removal of the catalyst in either retrofitted radial reactors or straight-flow integral reactors, and could offer reduced catalyst attrition due to abrasion than conventional pellets.

Finally, thin catalyst walls could limit the migration and loss of the potassium component of the catalyst, an effect which has been identified as a major cause of catalyst deactivation in catalyst beads. Ethylbenzene dehydrogenation catalysts typically comprise potassium salts, usually as carbonates, with the carbonate residue remaining after calcination and activation acting as an additional catalyst for the oxidation of coke in the presence of steam during reactor operation.

U.S. Pat. No. 4,711,930 discloses the use of honeycomb catalysts to reduce pressure drop in the ethylbenzene dehydrogenation process, but the catalyst mixtures provided in accordance with that patent are difficult to shape into honeycombs of the required low flow impedance, high catalyst activity, and chemical and mechanical durability (strength and attrition resistance) needed for conducting a stable commercial dehydrogenation process. One specific source of difficulty with these mixtures relates to a fundamental incompatibility between the chemical constituents required for catalyst formation and the vehicle systems required for shaping the catalysts into active yet durable honeycomb shapes.

SUMMARY OF THE INVENTION

This invention provides extruded honeycomb catalysts of high quality together with a method for extruding such catalysts in a thin-wall, high cell density configuration that preserves catalytic activity while enhancing the manufacturability and physical durability of the catalyst. The method is applicable to ethylbenzene dehydrogenation catalysts as well as a variety of other industrial-grade catalysts made from catalyst formulations that necessarily comprise relatively high concentrations of salts or other water-soluble catalyst constituents.

In a first aspect, then, the invention may be characterized as an improvement in the method of making a honeycomb catalyst by the extrusion of a plasticized catalyst precursor mixture including at least one water-soluble metallic salt catalyst precursor and a temporary organic binder through a honeycomb extrusion die. The improvements of the invention are secured through the use of a temporary organic binder that includes at least one highly-dispersed water-insoluble organic polymer in place of the water-soluble temporary binders more typically employed for the extrusion of inorganic honeycomb bodies.

The method of the invention comprises the initial step of preparing a honeycomb extrusion batch having a plasticity, lubricity, and viscosity suitable for forming a strong, green honeycomb. The batch is formulated from a catalyst precursor mixture that includes a substantial proportion of one or more water-soluble metallic catalyst precursors. This plasticized catalyst precursor mixture will comprise a water vehicle, at least one water-insoluble catalyst precursor, at least one water-soluble metallic salt catalyst precursor, and at least one temporary extrusion binder consisting essentially of a finely-divided water-insoluble organic polymer. Typically a plasticizer and a lubricant will also be included.

After combining and mixing these constituents for a time sufficient to achieve suitable plasticization of the catalyst precursor mixture, the plasticized mixture is extruded through a honeycomb die to form a green honeycomb. Providing appropriate proportions of water and temporary binders insures that green honeycomb bodies can be formed to closely prescribed honeycomb shapes, cell configurations, cell sizes and wall thicknesses at relatively low extrusion pressures and with excellent body integrity. Furthermore, the wet green honeycombs are sufficiently durable to resist deformation during handling and subsequent processing.

Following forming, the green honeycombs are dried and heat-treated to convert the catalyst precursors in the green honeycombs to the final catalyst. The characteristics of the temporary binder are such that drying and heat treatment can be carried out efficiently and with minimal processing losses.

The product of the above-described process is an improved honeycomb dehydrogenation catalyst of high activity and strength. For example, a typical ethylbenzene dehydrogenation catalyst is a durable honeycomb composed of an active potassium oxide (carbonate)-promoted, oxide-stabilized iron oxide catalyst with an axial crushing strength (parallel with the honeycomb channel axis) of at least 100 psi. Honeycomb geometries particularly appropriate for this particular catalyst, which may include honeycomb cell densities in the range of 15–400 cells/in 2 or more and channel wall thicknesses in the range of 0.2–3 mm, are readily obtained by this process.

DETAILED DESCRIPTION

A wide variety of different catalyst formulations for the dehydrogenation of ethylbenzene and similar feed stocks are known. Among the families of catalysts particularly suitable for ethylbenzene dehydrogenation are iron oxide catalysts containing ferric oxides, other transition metal oxides, potassium oxide, vanadium oxide, molybdenum and tungsten oxides, chromium oxide, aluminum oxide, cerium oxide, in addition to other rare earth oxides, and alkaline earth oxides. Known catalyst compositions for this dehydrogenation process include those comprising, when calculated as oxides, about 20–95 wt % of total of iron oxide, magnetite, or potassium ferrite yielding compounds, 0.1–40 wt % of potassium compounds, 0.1–30 wt % of cerium compounds, 0.1–30 wt % of molybdenum compounds, 0–25 wt % of Ca compounds, and 0–25 wt % of Mg compounds. One specific catalyst family of interest includes compositions comprising, in weight percent on an oxide basis, about 50–80% $Fe_2O_3$, 10–27% $K_2O$, 0–5% $Ce_2O_3$, 0–3% $MoO_3$, 0–3% CaO and 0–10% MgO. Of course, the invention is not limited to use with these specific families of catalysts but has utility for the production of other salt-derived catalyst honeycomb compositions as well.

U.S. Pat. No. 4,711,930 forms honeycombs from slurries containing mixtures of these materials, but the slurries present significant extrusion difficulties and the green honeycombs require very slow drying (several days) prior to calcination to temperatures in the 850° C. range. As a practical matter, we have found that the choice of organic materials to be included in such batches is largely determinative of the type and quality of the resulting extrudates, and in fact whether the resulting batch compositions can even be economically extruded to produce unitary, defect-free products.

Another important variable affecting extrudate quality during the extrusion process is the nature of the powder making up the solids component of the extrusion batch. In the case of iron-containing dehydrogenation catalysts of the kind hereinafter more fully described, a careful selection of the iron oxide powders that make up the major proportion of the extrusion batch can substantially improve extrusion results.

Particularly for honeycomb extrusion applications, powders having a particle size distribution that includes significant fractions of particles falling both above and below the median particle size of the material are preferred. Powders with bell-shaped particle size distributions, e.g. distributions wherein 5–15% of the particles fall into each of the bottom and top quartiles of the particle size distribution range, are examples of useful powders. In the case of iron oxide-based extrusion batches specifically, the inclusion of major iron oxide additions that do not have a relatively broad particle size distribution can result in poor batch rheology and reduced extrudate quality.

Also important is the median particle size of the solids component of the extrusion batch. In general a batch (e.g. iron oxide) median particle size below 0.3 $\mu$m can cause extrusion problems, whereas batches having bell-shaped particle size distributions with median particle sizes in the range of 0.3–4 $\mu$mean produce excellent results. Of course, bimodal or multimodal particle size distributions offering a good range of particle sizes, prepared for example by mixing iron oxides of various distributions to facilitate particle packing, can also promote stiff yet plastic batch rheology and thereby contribute to high quality extrusions and good calcined honeycomb strength.

Ethylbenzene dehydrogenation catalysts as well as certain other catalysts of similar type are highly basic mixtures, and precursors useful for providing high catalyst activity often comprise high concentrations of salts or other water-soluble ingredients. Potassium carbonate and ammonium molybdate are examples of soluble materials that may be included in such mixtures.

Conventional water-soluble extrusion binders such as methylcellulose, polyethylene oxide, or other polyelectrolyte binders are prone to precipitation or degradation in aqueous solutions of these materials. The result is often a phase separation between the water and the solids component of the batch that interferes significantly with honeycomb forming through extrusion dies and thus substantially degrades extrudate quality. Extrusion back-pressures tend to exacerbate any water separation that may occur, making forming difficult or impossible. These effects are particularly pronounced where honeycomb cell densities in excess of 100 cells per square inch (cpsi) are needed, causing losses of batch plasticity that can completely prevent web knitting from occurring.

Likewise, starches are not generally useful as binders in these catalyst systems. Most starches have low solubility in water below 50° C. and thus must be used in large concentrations to provide effective binding and green strength. Long mixing times are generally required, and large starch concentrations, if used, can extend drying times to intervals of several days instead of several hours. In addition, starches can absorb water and swell on heating, increasing the probability of honeycomb cracking as the honeycombs are heated for drying and calcining.

The catalyst extrusion batches of the invention are prepared by mixing the solid catalyst precursors together with specific organic extrusion aids that act as both a binder for the mixture and a source of plasticity and lubricity for the extrusion process. These binders may be generally characterized as water-insoluble organic binders that do not interact adversely with salts in the extrusion batch, but instead become strong binders for the catalyst precursors even at high pH levels. The most desirable water-insoluble binders also provide excellent extrusion characteristics, either alone or in combination with additional plasticizer-lubricants, to further reduce extrusion pressures and assure the formation of high quality honeycombs. The result is excellent web knitting through the die-land as the batch is extruded, so that a well-integrated honeycomb structure is formed.

Among the binder formulations providing particularly high green strength at relatively low concentrations in the catalyst extrusion batches are latex emulsions. Specific examples of such emulsions are colloidal acrylic, acrylic-styrene, vinyl-acrylic, and urethane-acrylic emulsions. The use of low binder concentrations is important for honeycomb production since binder decomposition reactions and/or large exotherms which might otherwise causing cracking of the honeycomb parts during calcination can thereby be minimized or avoided.

While not intending to be bound by theory, it is presently thought that the water-insoluble nature of these acrylic or other latex binders, which are typically colloidal in nature, imparts greater salt tolerance to the binders. In addition, some of the acrylic latex binders appear to exhibit desirable heat-activated gelling behavior in those catalyst precursor mixtures of higher pH.

The advantages of gelling behavior are well illustrated by certain ethylene dehydrogenation catalyst precursor batches, some of which can have pH values greater than 9 with water as the main vehicle. Since the gelling effect is accelerated by heat, drying catalysts extruded from these batches in an oven at moderate temperatures (e.g., <100° C., preferably 75–85° C.) quickly sets and dries the honeycomb. Even at these temperatures setting can occur within ten minutes and drying may be completed within an hour. This is particularly useful in the case of thin-wall, high-cell-density honeycomb structures, since rapid setting greatly diminishes the incidence of wet green honeycomb deformation.

On the other hand, premature gelling of the precursor batches, for example gelling occurring during the mixing or extrusion of the batch, can interfere with proper forming. Gelling behavior in acrylic binder systems appears to be related to the glass transition temperature $T_g$ of the acrylic selected, with latex binder formulations comprising softer acrylics being more likely to gel at lower temperatures in these batches than latex formulations containing acrylics with higher transition temperatures. For this reason, acrylic binder formulations comprising acrylics with $T_g$ values sufficiently above ambient (25° C.) to avoid gelling during mixing or extrusion will normally be preferred, if only to avoid the need to prevent or minimize batch heating during processing.

The catalyst batches of the invention may also include additional plasticizers, lubricants and extrusion aides to facilitate the plasticization and forming processes, provided the additives are compatible (do not harmfully interact) with the binder emulsions employed during mixing, drying or calcining. Some compounds can function as both a plasticizer and a lubricant in the batch. Examples of particularly suitable batch additives include polyalkylene glycols such as polyethylene glycol (PEG), which are fully compatible with many latex emulsions and act to both plasticize and lubricate the batch. Additional lubricants may include organic salts and acids, such as alkali stearate, ammonium stearate, stearic acid. Soluble members of these groups, e.g., sodium stearate, can interact with polyalkylglycols to cross-link and form a gel, yielding beneficial rheology.

Honeycombs of various geometries, including round, square, hexagonal, triangular, and others, of uniform or mixed cell size and wall thickness can be easily extruded from the described batch mixtures, and can be dried and calcined quickly without cracking. Extrusion web thicknesses within a preferred range of 0.5–1.5 mm and cell densities in a preferred range of 25–200 cpsi can readily be formed from these batches utilizing conventional honeycomb extrusion equipment.

The invention may be further understood by reference to the following detailed examples, both with and without acrylic binders, which are intended to be illustrative rather than limiting.

EXAMPLE 1

Catalyst Preparation

Two honeycomb catalysts having iron-oxide compositions of known suitability for ethylbenzene dehydrogenation are prepared for testing. The batches are prepared by combining appropriate proportions of catalyst precursors with a water vehicle, a latex emulsion binder, and a polyethylene glycol plasticizer/lubricant according to the following procedure.

For each of the catalysts, hereinafter referred to as Catalysts A and B, a measured portion of fine iron oxide powder, obtained as red $\alpha$-$Fe_2O_3$ and having a median particle size of about 2.8 $\mu$m with 80% of the particles falling in the 1.9–4.5 $\mu$m size range, is placed in a mixing container and other dry catalyst precursors are combined therewith. The other precursors consist of ammonium heptamolybdate and the carbonate salts of potassium, cerium, and magnesium, each of these being added to the iron oxide powder in proportions calculated to provide the oxide concentrations (in parts by weight) reported in Table 1 below, after calcination of the precursors to convert the salts to oxides. The dry mixture is agitated in a turbular mixer.

TABLE 1

Catalyst Batches

| Catalyst Component | Catalyst Composition (as oxides) | |
|---|---|---|
|  | Catalyst A (JP) | Catalyst B (JQ) |
| $Fe_2O_3$ | 70 | 77 |
| $K_2O$ | 16 | 10 |
| $Ce_2O_3$ | 5 | 5 |
| $MoO_3$ | 1.3 | 3 |
| CaO | — | 2 |
| MgO | 7 | 2 |

For each 100 parts by weight of each dry precursor mixture prepared as above described, 10 parts by weight of a water vehicle are mixed with 2 parts by weight of polyethylene glycol (PEG) liquid (average glycol molecular weight of 400) and the glycol-water mixture is poured slowly onto the dry ingredients for mulling. Thereafter, an addition of 4 parts by weight (based on the dry precursor weight) of a stabilized aqueous acrylic emulsion (acrylic latex) is slowly made to each batch mixture. This emulsion is stable at a pH of 2.7 and comprises 30 wt % of an acrylic colloid having an average particle size of 80 nm and a glass transition temperature of 81° C.

Choosing an acrylic colloid with a glass transition temperature near the drying temperature in accordance with this procedure appears to significantly enhance binding effectiveness during drying. It is thought that, as the acrylic softens under drying conditions, it becomes more susceptible to interactions with the basic (pH>8) batch. Strong polymeric associations, cross-linking, and other interactions of the acrylic colloid can then occur which could be responsible for the observed binder strengthening effect.

Following mixing, additional water is added to each batch to adjust batch viscosity to a convenient level for plasticizing and extruding, the additional water bringing the total water content of each batch to about 16% by weight. Each batch is then further mixed and sheared in a low-shear (muller) mixer to provide a homogeneous plastic catalyst precursor batch.

The resulting batches are promptly extruded through conventional "spaghetti"-type dies to improve homogeneity and facilitate plasticization. The spaghetti extrudate is then itself extruded through a conventional square-celled honeycomb extrusion die having criss-crossing honeycomb discharge slots of 0.025 inches width forming a cell wall network providing about 100 square cells per square inch of honeycomb cross-sectional area. Well-formed green honeycomb extrudate is produced by this process at extrusion pressures well within the limits imposed by the extruder and extrusion die.

To promote rapid stiffening of the honeycomb extrudate, the extruding honeycomb material is exposed to hot air after it emerges from the die, and is then cut into sections to facilitate further handling. The stiffened honeycomb sections are then placed in an air oven operating at 80° C. for approximately 40 minutes for drying. The dried honeycombs are then debindered at 300° C. for 2 hours and calcined at 850° C. for 6 hours to convert the salts present in the green honeycombs to their respective oxides. The dried and calcined honeycombs are substantially free of extrusion and drying defects and have an A-axis crushing strength of 1600 psi, with the calcined oxide mixture forming the honeycomb walls having a surface area of 4 $m^2/g$ as determined by nitrogen BET measurements.

EXAMPLE 2

Comparative

To 100 parts by weight of each of a Catalyst A and Catalyst B mixture prepared as described above in Table 1 above, 2 parts of sodium stearate are added. The resulting batches with stearate additives are then blended in a turbular mixer, and a vehicle comprising 10 parts by weight of water and 4 parts by weight of polyethylene glycol liquid (average glycol molecular weight of 400) for each 100 parts by weight of the dry catalyst/stearate mixtures is poured slowly onto each of the dry mixtures for mulling.

Following mulling, additional water is added to each of the batches to adjust batch viscosity to a convenient level for plasticizing and extruding. The additional water brings the total water content of each batch to about 16% by weight. Each batch thus provided is then further mixed and sheared in a low-shear muller mixer to develop a homogeneous plastic catalyst precursor batch, and the batches are then promptly extruded through a conventional spaghetti die to further improve homogeneity and facilitate plasticization.

Without the acrylic latex binder, these plasticized batches are found to be quite brittle and to exhibit rather low plasticity, with the extrudate tending to separate into small pieces during the spaghetti extrusion. The separating extrudates are, however, amenable to shaping at reasonable extrusion pressures into well-formed green honeycombs if promptly re-extruded through conventional square-celled honeycomb extrusion dies having crisscrossing honeycomb discharge slots of 0.025 inches width forming 100 square cells per square inch of honeycomb cross-sectional area.

As in Example 1, rapid stiffening of the honeycombs with hot air after extrusion permits the honeycomb extrudate to be cut into lengths for subsequent handling. However, even after drying in air at 80° C. for approximately 40 minutes, the resulting dry honeycombs brittle and relatively weak, this result being attributable to the absence of the acrylic latex binder from the binder system. The PEG and sodium stearate vehicle components provide acceptable extrusion rheology but relatively low plasticity and green strength, a circumstance which would plainly adversely impact production yields.

However, if calcined at 850° C. for 6 hours to convert the salts present in the green honeycombs to their respective oxides, the dried and calcined honeycombs are found to be substantially free of extrusion and drying defects, with an A-axis crushing strength of 1600 psi and a wall surface porosity of about 4 $m^2/g$ as determined by nitrogen BET testing.

EXAMPLE 3

Separate extrusion batches for each of Catalyst A and Catalyst B reported above in Table 1 are prepared as described in Example 1 above, except that the water/PEG vehicle employed in each batch contains 4 parts by weight of the 400 molecular weight polyethylene glycol mulling addition rather than the 2 parts by weight PEG used in Example 1.

Following the addition of the stabilized aqueous acrylic emulsion and additional batch water to reach a total water content of 16% by weight, the batches are plasticized, pre-extruded through a spaghetti die, and then extruded through the 100 cpsi honeycomb die. The final extrusion produces well-formed honeycomb extrudates with excellent green strength that can be dried and fired at high yields to provide strong, substantially defect-free catalyst honeycombs.

EXAMPLE 4

Catalytic Activity

To test the activity of the honeycomb catalysts produced as above described, a honeycomb sample having the composition of Catalyst A above with a length of about 10 cm, a diameter of about 2.5 cm, and a weight of about 50 g is tested for dehydrogenation activity in a fixed bed reactor configuration. The honeycomb catalyst is loaded into a 1" quartz tube reactor vessel and ethylbenzene and de-ionized water are introduced into the top of the reactor, vaporized, and flowed downwardly as a mixed vapor stream through the honeycomb catalyst sample. The reacted effluent stream is cooled down below room temperature so that the liquid products are separated from the gas stream in a static separator. The reaction is carried out under atmospheric pressure and steady-state conditions. The liquid product of the reaction is clear.

Table 2 below lists representative conversion efficiencies and selectivities for the conversion of ethylbenzene (EB) to styrene at a number of different reaction conditions carried out over a period of several days.

EXAMPLE 5

Catalytic Activity

A sample of honeycomb Catalyst B, having the same dimensions as the Catalyst A sample of Example 2 but with a weight of about 59.2 g, is subjected the same testing procedure described in that Example. Representative results for such activity testing are reported in Table 3 below. In the case of Catalyst B, about 69% EB conversion with 93% selectivity for styrene production are observed at a liquid hour space velocity of 0.48 per hour and an average bed temperature of 607° C. Thus this catalyst demonstrates stable activity good conversion efficiency for the conversion of ethylbenzene to styrene.

TABLE 2

Catalytic Activity - Honeycomb Catalyst A

| Test Day | Time On-Stream (hrs) | LHSV ($hr^{-1}$) | WHSV ($hr^{-1}$) | Ratio $H_2$/EB (wt/wt) | Average Bed Temp (° C.) | EB Conversion (wt %) | Selectivity To Styrene (wt %) | Phenylacetylene Content (ppm-wt) |
|---|---|---|---|---|---|---|---|---|
| 1 | 4    | 0.48 | 0.42 | 2.31 | 605.8 | 71.81 | 91.47 | NA  |
| 1 | 7    | 0.48 | 0.42 | 2.31 | 608.9 | 73.27 | 91.58 | 196 |
| 2 | 31.5 | 0.48 | 0.42 | 2.31 | 608.2 | 75.03 | 90.72 | 160 |
| 3 | 52   | 0.48 | 0.42 | 2.31 | 608.5 | 76.11 | 90.69 | NA  |
| 5 |      | 0.48 | 0.42 | 2.31 | 581.0 | 59.48 | 95.51 | 65  |
| 7 |      | 0.48 | 0.42 | 2.31 | 587.8 | 68.16 | 93.45 | 84  |

As is evident from a study of the data presented in Table 2 above, about 75% conversion of ethylbenzene with approximately 91% selectivity for conversion to styrene may be obtained with this catalyst at a catalyst bed temperature of 608° C. and a liquid hour space velocity (LHSV) of 0.48 per hour. In general, higher bed temperatures favor increased conversion efficiency, but styrene selectivity increases somewhat at lower bed temperatures. The clarity of the liquid reaction product at all reaction temperatures suggests high product quality. Thus Catalyst A provides a stable and active catalyst for ethylbenzene dehydrogenation reaction.

TABLE 3

Catalytic Activity - Honeycomb Catalyst B

| Test Day | Time On-Stream (hrs) | LHSV ($hr^{-1}$) | WHSV ($hr^{-1}$) | Ratio $H_2O$/EB (wt/wt) | Average Bed Temp (° C.) | EB Conversion (wt %) | Selectivity To Styrene (wt %) | Phenylacetylene Content (ppm-wt) |
|---|---|---|---|---|---|---|---|---|
| 1 | 6   | 0.48 | 0.35 | 2.31 | 608.3 | 66.19 | 93.84 | NA  |
| 1 | 8.5 | 0.48 | 0.35 | 2.31 | 608.7 | 67.19 | 94.01 | 130 |
| 2 | 27  | 0.48 | 0.35 | 2.31 | 606.9 | 68.63 | 94.02 | 126 |
| 2 | 32  | 0.48 | 0.35 | 2.31 | 607.3 | 69.12 | 94.03 | 123 |
| 3 | 48  | 0.48 | 0.35 | 2.31 | 607.5 | 69.65 | 93.71 | 108 |
| 3 |     | 0.48 | 0.35 | 2.31 | 591.2 | 60.13 | 94.82 | 73  |
| 3 |     | 0.48 | 0.35 | 2.31 | 591.1 | 60.25 | 94.81 | 122 |

EXAMPLE 6

For the extrusion of honeycomb catalysts of higher honeycomb cell density, a catalyst extrusion batch of somewhat higher stiffness than utilized in Example 1 above may be prepared. The same general mixing, mulling and plasticizing steps of the process are followed, but the amount polyethylene glycol/water mixture is reduced to 1 wt % of batch to decrease batch softness, and the batch is sheared for a longer time prior to extrusion to achieve batch plasticization. Extrusion of this stiffer batch through extrusion dies of 200 and 400 cells per square inch of honeycomb cell density having discharge slots of 0.15 mm width readily yields honeycomb extrudate of high structural integrity. And, the honeycomb shapes can be dried within 40 minutes and calcined at 850° C. over a period of several hours to yield strong honeycomb catalysts substantially free of drying and calcining defects.

We claim:

1. A plasticized honeycomb extrusion batch for a dehydrogenation catalyst which comprises:

a powder component comprising iron oxide and a water-soluble alkali metal salt promoter;

at least one colloidal dispersion of a water insoluble polymer binder;

at least one plasticizer at least one lubricant; and a water vehicle.

2. A plasticized batch in accordance with claim 1, wherein the water insoluble polymer binder is a polymer selected from the group consisting of acrylic, styrene-acrylic, vinyl-acrylic, and urethane-acrylic polymers, copolymers, terpolymers, and thermoplastics.

3. A plasticized batch in accordance with claim 1, wherein the plasticizer or lubricant is selected from the group consisting of polyethylene glycols, acrylic acids, acrylates, polyvinyl alcohols, organic salts, and other organic acids.

4. A plasticized batch in accordance with claim 1, which includes water in a proportion of about 15–20 wt % of the batch solids content.

5. A method of making a honeycomb dehydrogenation catalyst which comprises the steps of:

compounding a catalyst batch comprising at least one water-insoluble catalyst precursor, at least one water-soluble metallic salt catalyst precursor, at least one finely-divided water-insoluble organic polymer, and a water vehicle;

plasticizing the batch;

extruding the plasticized batch through a honeycomb extrusion die to form a honeycomb shape;

drying the extruded honeycomb shape; and heat-treating the dried honeycomb shape to form a calcined honeycomb catalyst.

6. An extruded honeycomb dehydrogenation catalyst having a body consisting essentially of a potassium oxide (carbonate)-promoted oxide-stabilized iron oxide catalyst, a honeycomb cell density in the range of 15–400 channels per square inch, a channel wall thickness in the range of 0.2–3 mm, and an axial crushing strength in excess of 100 psi., said catalyst being produced by firing an extruded honeycomb preform comprising iron oxide, a potassium salt, a colloidal water-insoluble organic polymer, and a water vehicle.

7. A honeycomb catalyst in accordance with claim 6 having a composition comprising, in weight percent when calculated as oxides, about 20–95 wt % total of iron oxide, magnetite, and potassium ferrite-yielding compounds, 0.1–40 wt % total of potassium compounds, 0.1–30 wt % of cerium compounds, 0.1–30 wt % of molybdenum compounds, 0–25 wt % of calcium compounds, and 0–25 wt % of magnesium compounds.

8. A honeycomb catalyst in accordance with claim 6 having a honeycomb channel density in the range of about 25–200 channels per square inch and a honeycomb channel wall thickness in the range of about 0.5–1.5 mm, and a surface area of 0.5 to 20 $m^2/g$.

9. An extruded honeycomb dehydrogenation catalyst having a composition comprising, in weight percent when calculated as oxides, about 20–95 wt % total of iron oxide, magnetite, and potassium ferrite-yielding compounds, 0.1–40 wt % total of potassium compounds, 0.1–30 wt % of cerium compounds, 0.1–30 wt % of molybdenum compounds, 0–25 wt % of calcium compounds, and 0–25 wt % of magnesium compounds, a honeycomb cell density in the range of 15–400 channels per square inch, a channel wall thickness in the range of 0.2–3 mm, and an axial crushing strength in excess of 100 psi., said catalyst being produced by firing an extruded honeycomb preform comprising iron oxide, a potassium salt, a colloidal water-insoluble organic polymer, and a water vehicle.

* * * * *